US008623097B2

(12) United States Patent
Gerold et al.

(10) Patent No.: US 8,623,097 B2
(45) Date of Patent: Jan. 7, 2014

(54) IMPLANT SYSTEM HAVING A FUNCTIONAL IMPLANT COMPOSED OF DEGRADABLE METAL MATERIAL

(75) Inventors: Bodo Gerold, Zellingen (DE); Bjoern Klocke, Zurich (CH); Matthias Fringes, Ansbach (DE)

(73) Assignee: Biotronik VI Patent AG, Baar (CH)

( * ) Notice: Subject to any disclaimer, the term of this patent is extended or adjusted under 35 U.S.C. 154(b) by 238 days.

(21) Appl. No.: 12/499,137

(22) Filed: Jul. 8, 2009

(65) Prior Publication Data

US 2010/0010640 A1  Jan. 14, 2010

(30) Foreign Application Priority Data

Jul. 8, 2008  (DE) .................... 10 2008 040 253

(51) Int. Cl.
*A61F 2/48* (2006.01)
*A61B 17/68* (2006.01)

(52) U.S. Cl.
USPC ............................................. 623/24; 606/60

(58) Field of Classification Search
USPC ................... 623/24, 23.75, 16.11; 606/60
See application file for complete search history.

(56) References Cited

U.S. PATENT DOCUMENTS

| | | | | |
|---|---|---|---|---|
| 4,519,394 A * | 5/1985 | Black et al. | ...................... | 607/50 |
| 6,875,208 B2 * | 4/2005 | Santini et al. | .............. | 604/890.1 |
| 7,041,130 B2 * | 5/2006 | Santini et al. | ................. | 623/1.42 |
| 7,101,642 B2 * | 9/2006 | Tsukamoto et al. | .......... | 429/245 |
| 7,368,190 B2 * | 5/2008 | Heller et al. | ....................... | 429/2 |
| 7,657,297 B2 * | 2/2010 | Simpson et al. | .............. | 600/347 |
| 7,879,367 B2 * | 2/2011 | Heublein et al. | .............. | 424/682 |
| 2006/0052782 A1 | 3/2006 | Morgan et al. | | |
| 2006/0271168 A1 | 11/2006 | Kleine et al. | | |
| 2007/0055305 A1 * | 3/2007 | Schnyder et al. | ............. | 606/221 |
| 2007/0239260 A1 | 10/2007 | Palanker et al. | | |
| 2008/0015578 A1 | 1/2008 | Erickson et al. | | |
| 2008/0044721 A1 * | 2/2008 | Heller et al. | ..................... | 429/43 |
| 2008/0058772 A1 * | 3/2008 | Robertson et al. | .......... | 604/890.1 |
| 2008/0118782 A1 * | 5/2008 | Heller et al. | ....................... | 429/2 |

(Continued)

FOREIGN PATENT DOCUMENTS

| | | |
|---|---|---|
| EP | 0966979 A2 | 12/1999 |
| WO | WO 8102668 A * | 10/1981 |

(Continued)

OTHER PUBLICATIONS

Search Report for German Patent Application No. 10 2008 040 253.2; Apr. 23, 2009.
Search Report for European Patent Application No. 09162534.3; Oct. 29, 2009.

*Primary Examiner* — Suzette J Gherbi
(74) *Attorney, Agent, or Firm* — Greer, Burns & Crain Ltd.

(57) ABSTRACT

An implant system comprising a functional implant (5, 6) that fulfills a medical function, particularly a bone implant, which is formed at least in part of a metal material that can be degraded by the body (2) of the implant wearer, as well as a control device (7) for controlling the degradation behavior of the functional implant (5, 6). The control device (7) has a counter-electrode (10) to the functional implant (5, 6), and a voltage source (8) for making available a polarization voltage (ΔU) between functional implant (5, 6, 15) and counter-electrode (10), to control the degradation behavior of the functional implant (5, 6).

20 Claims, 4 Drawing Sheets

(56) References Cited

U.S. PATENT DOCUMENTS

| | | | |
|---|---|---|---|
| 2008/0249638 A1* | 10/2008 | Asgari | 623/23.75 |
| 2009/0081313 A1* | 3/2009 | Aghion et al. | 424/641 |
| 2009/0297581 A1* | 12/2009 | Atanasoska et al. | 424/423 |
| 2010/0042205 A1* | 2/2010 | Atanasoska et al. | 623/1.38 |
| 2010/0159570 A1* | 6/2010 | Feldman et al. | 435/286.1 |
| 2010/0168501 A1* | 7/2010 | Burnett et al. | 600/13 |
| 2010/0211186 A1* | 8/2010 | Senders et al. | 623/24 |
| 2012/0065726 A1* | 3/2012 | Atanasoska et al. | 623/1.38 |

FOREIGN PATENT DOCUMENTS

| | | | |
|---|---|---|---|
| WO | WO 8102668 A1 * | 10/1981 | A61F 1/00 |
| WO | 0154617 A1 | 8/2001 | |
| WO | 2007070790 A2 | 6/2007 | |
| WO | 2008013879 A2 | 1/2008 | |
| WO | 2008030634 A1 | 3/2008 | |

* cited by examiner

IMPLANT SYSTEM HAVING A FUNCTIONAL IMPLANT COMPOSED OF DEGRADABLE METAL MATERIAL

PRIORITY CLAIM

This patent application claims priority to German Patent Application No. 10 2008 040 253.2, filed Jul. 8, 2008, the disclosure of which is incorporated herein by reference in its entirety.

FIELD

The present disclosure relates to an implant system comprising a functional implant that fulfills a medical function, which implant is formed at least in part by a metal material that can be degraded by the body of the implant wearer.

BACKGROUND

Implants are used for therapy of bone fractures, for example, in the form of nails, screws, or plates. Fundamentally, the process that occurs in the body when the broken ends of bones grow together is supposed to proceed with as little disruption as possible and in regular anatomical manner. In this connection, the most usual method is the use of an immobilization bandage in the form of a plaster or plastic cuff. This is generally used for uncomplicated fractures. The disadvantage of this method is the long loss of function of the injured extremity, leading to muscle and bone degeneration (atrophy) if the period of non-use is a long one.

In order to prevent atrophy, and in order to be able to begin rehabilitation as early as possible, it is increasingly true that an operation is carried out in the case of bone fractures wherein more precise restoration of the anatomy and better fixation of the fragments are possible using nails, screws, or plates. For older patients, this is often the only possibility so that the patients do not lose their previous independence for a long period of time or even permanently.

Usually, such functional implants for support, fixation, and hold are produced from non-degradable materials, such as medical steel or titanium (alloys). After the bone fragments have grown together, these implants remain in the body or they are explanted during the course of another operation.

Functional implants that remain in the body can lead to irritations, such as inflammations, in the long term. Explantation of the implant leads to another avoidable operation.

In order to provide a remedy here, orthopedic implants are known, for example, from U.S. Patent Publication No. 2008/0015578, which are produced at least in part from metal materials that can be degraded by the body of the implant wearer. Metals, such as iron, magnesium, zinc, tungsten, as well as mixtures or alloys of these, are used.

An active orthopedic implant, for example, in the form of a bone plate, is known from U.S. Patent Publication No. 2006/0052782, which has at least one microchip and a sensor connected with it. The sensor responds to physical signals from the implant or from the patient tissue, such as temperature, pressure, or tensile stress, for example. The data recorded by the sensor are processed by the microchip and transmitted to a receiver disposed outside of the patient, such as a personal computer, for example. In this way, the medical care personnel can undertake a diagnosis, for example, of the effective period of functioning of the implant, the stress on the bone plate, and possible complications that can occur in the case of orthopedic implants, in the form of infections, non-healing of the fracture, and fatigue. Furthermore, the implant can have electrodes on its surface to support the healing process of the bone fracture.

A disadvantage of functional implants composed of a degradable material is the fact that the degradation process is dependent on the conditions in the body of the implant wearer, in each instance. In particular, the degradation process cannot be actively influenced.

SUMMARY

The present disclosure describes several exemplary embodiments of the present invention.

One aspect of the present disclosure provides an implant system, comprising a) a medical implant formed at least in part from a metal material that can be degraded by the body of the implant wearer, and b) a control device for controlling the degradation behavior of the functional implant, the control device having (i) at least one counter-electrode to the functional implant, and (ii) a voltage source for making available a polarization voltage ($\Delta U$) between functional implant and counter-electrode, to control the degradation behavior of the functional implant.

The present disclosure is based on the task of indicating an implant system of the type stated, in which the degradation process, particularly the point in time at which it starts, and its duration, can be actively influenced.

This task is accomplished by an implant system having a functional implant that fulfills a medical function, particularly a bone implant, vascular support, stent, or depot implant, which is formed at least in part by a metal material that can be degraded by the body of the implant wearer. A control device for controlling the degradation behavior of the functional implant is provided having a counter-electrode with regard to the functional implant, which electrode consists of an electrochemically more precious metal material as compared with the metal material of the functional implant, and having a voltage source for making available a polarization voltage between functional implant and counter-electrode to control the degradation behavior of the functional implant.

Using this control device, it is possible to control the degradation behavior of the functional implant in a targeted manner, in that the polarization voltage applied between the functional implant and the counter-electrode protects the functional implant cathodically and thus it does not degrade, or at least the implant degrades more slowly. Thus, the dissolution of the implant after insertion can be delayed at first or completely prevented. As soon as the support, fixation, or hold function of the implant has been fulfilled, degradation of the implant can be accelerated by means of applying the polarization voltage using the control device.

For purposes of the present disclosure, the term "functional implants" comprises vascular supports, stents, or depot implants. Areas of application for the functional implants are also urological, intracranial, vascular, and orthopedic applications, local-drug-delivery applications, as well as applications in cancer therapy.

Preferably, at least one reference electrode is provided to determine the voltage actually applied to the functional implant (5, 6, 15).

According to one exemplary embodiment, the control device has an implantable battery as a voltage source. Such a power source is reliable and extremely inexpensive.

Other exemplary embodiments of the implant system relate to the design of the counter-electrode, which can be separately implantable or formed by the housing of the implantable control device itself. If the counter-electrode is configured separately, the counter-electrode can consist of a degradable metal material, but the metal material must be electrochemically more precious than the metal material of the functional implant. Then, the counter-electrode no longer has to be explanted because the counter-electrode degrades over time, even in the body of the implant wearer.

If the counter-electrode is formed by the housing of the control device or its battery, a non-degradable material selection must be made, such as a titanium housing, for example. Optionally, complete or partial coating of the housing surface with a non-degradable metal, such as platinum, or a non-degradable alloy, such as platinum-iridium, can take place.

According one exemplary embodiment, switchability of the voltage source can be implemented in that a physician cuts the line connection between the battery and the counter-electrode, or explants the battery itself, during an outpatient operation. More convenient activation of the control device is possible; however, if the control device has a telemetrical data transmission unit, as is already the usual technology in the field of heart pacemakers. Control data for controlling the polarization voltage generated by the voltage source can be transmitted by way of the telemetrical data transmission unit, as can measurement data concerning the status of the functional implant, such as its degree of degradation, for example. In this way, true Home Monitoring can be implemented also in connection with the implant systems according to the present disclosure. Up to the present, it has not been known for orthopedic implants that their status or the status of the treated location can be monitored and influenced even without a visit to the doctor.

An implementation that is also covered by the general core of the present disclosure is implementation of the functional implant as a depot implant that has at least one depot chamber filled with a therapeutic agent. Using the control device disclosed herein, the depot chamber, which consists at least partly of a degradable metal material, can be degraded under time control and thus the therapeutic agent contained in the depot chamber can be released in a manner defined over time. By using multiple depot chambers and different materials or dimensions for their covers, release of different therapeutic agents, offset over time, can be controlled in connection with a defined polarization voltage applied by the control unit.

Anti-proliferative, anti-inflammatory and/or anti-mycotic active substances can be selected from, for example, the following list of substances:
abciximab, acemetacin, acetylvismion B, aclarubicin, ademetionin, adriamycin, aescin, afromoson, akagerin, aldesleukin, amidoron, aminoglutethemid, amsacrin, anakinra, anastrozol, anemonin, anopterin, anti-mycotics, anti-thrombotics, apocymarin, argatroban, aristolactam-AII, aristolochic acid, ascomycin, asparaginase, aspirin, atorvastatin, auranofin, azathioprin, azithromycin, baccatin, bafilomycin, basiliximab, bendamustin, benzocaine, berberin, betulin, betulic acid, bilobol, bisparthenolidin, bleomycin, bombrestatin, boswellic acids and their derivatives, bruceanole A, B and C, bryophyllin A, busulfan, anti-thrombin, bivalirudin, cadherine, camptothecin, capecitabin, o-carbamoyl phenoxy acetic acid, carboplatin, carmustin, celecoxib, cepharantin, cerivastatin, CETP inhibitors, chlorambucil, chloroquine phosphate, cictoxin, ciprofloxacin, cisplatin, cladribin, clarithromycin, colchicine, concanamycin, coumadin, C-Type Natriuretic Peptide (CNP), cudraisoflavon A, curcumin, cyclophosphamide, cyclosporin A, cytarabin, dacarbazin, daclizumab, dactinomycin, dapson, daunorubicin, diclofenac, 1,11-dimethoxycanthin-6-one, docetaxel, doxorubicin, dunaimycin, epirubicin, epothilone A and B, erythromycin, estramustin, etobosid, everolimus, filgrastim, fluro-blastin, fluvastatin, fludarabin, fludarabin-5'-dihydrogen phosphate, fluorouracil, folimycin, fosfestrol, gemcitabin, ghalakinoside, ginkgol, ginkgolic acid, glycoside 1a, 4-hydroxyoxycyclophosphamide, idarubicin, ifosfamide, josamycin, lapachol, lomustin, lovastatin, melphalan, midecamycin, mitoxantron, nimustin, pitavastatin, pravastatin, procarbazine, mitomycin, methotrexate, mercaptopurin, thioguanin, oxaliplatin, irinotecan, topotecan, hydroxycarbamide, miltefosin, pentostatin, pegasparase, exemestan, letrozol, formestan, SMC-Proliferation-Inhibitor-2w, mitoxanthrone, mycophenolatmofetil, c-myc-antisense, β-myc-antisense, β-lapachon, podophyllotoxin, podophyllic acid 2-ethylhydrazide, molgramostim (rhuGM-CSF), peginterferon α-2b, lanograstim (r-HuG-CSF), macrogol, selectin (cytokine antagonist), cytokine inhibitors, COX-2 inhibitor, NFkB, angiopeptin, monoclonal antibodies that inhibit muscle cell proliferation, bFGF antagonists, probucol, prostaglandins, 1-hydroxy-11-methoxycanthin-6-one, scopolectin, NO donors such as pentaerythrityl tetranitrate and syndnoeimines, S nitroso derivatives, tamoxifen, staurosporin, β-estradiol, α-estradiol, estriol, estron, ethinylestradiol, medroxyprogesterone, estradiol cypionates, estradiol benzoates, tranilast, kamebakaurin and other terpenoids that are used in cancer therapy, verapamil, tyrosine kinase inhibitors (tyrphostines), paclitaxel and its derivatives such as 6-α-hydroxy-paclitaxel, taxoteres, carbon suboxide (MCS) and its macrocyclic oligomers, mofebutazone, lonazolac, lidocaine, ketoprofen, mefenaminic acid, piroxicam, meloxicam, penicillamine, hydroxychloroquine, sodium aurothiomalate, oxaceprol, β-sitosterin, myrtecaine, polidocanol, nonivamid, levomenthol, ellipticin, D-24851 (commercially available from Calbiochem), colcemid, cytochalasin A-E, indanocin, nocadazole, S 100 protein, bacitracin, vitronectin receptor antagonists, azelastin, guanidylcyclase stimulator tissue inhibitor of metal proteinase-1 and 2, free nucleic acids, nucleic acids incorporated into virus transmitters, DNA and RNA fragments, plasminogen activator inhibitor-1, plasminogen activator inhibitor-2, antisense oligonucleotides, VEGF-inhibitors, IGF-1, active substances from the group of antibiotics such as cefadroxil, cefazolin, cefaclor, cefotixin, tobramycin, gentamycin, penicillins such as dicloxacillin, oxacillin, sulfonamides, metronidazol, enoxaparin, desulfated and N-reacetylated heparin (HEMOPARIN®), tissue plasminogen activator, GpIIb/IIIa platelet membrane receptor, Factor $X_a$-Inhibitor antibodies, heparin, hirudin, r-hirudin, PPACK, protamine, prourokinase, streptokinase, warfarin, urokinase, vasodilators such as dipyramidol, trapidil, nitroprussides, PDGF antagonists such as triazolopyrimidine and seramine, ACE inhibitors such as captopril, cilazapril, lisinopril, enalapril, losartan, thioprotease inhibitors, prostacyclin, vapiprost, interferon α, β and γ, histamine antagonists, serotonin blockers, apoptose inhibitors, apoptose regulators such as p65, NF-kB or Bcl-xL antisense oligonucleotides, halofuginon, nifedipin, tocopherol, tranilast, molsidomin, tea polyphenols, epicatechine gallate, epigallocatechine gallate, leflunomide, etanercept, sulfasalazine, etoposide, dicloxacillin, tetracycline, triamcinolon, mutamycin, procainimide, retinolic acid, quinidine, disopyrimide, flecainide, propafenon, sotolol, naturally and synthetically produced steroids such as inotodiol, maquirosid A, ghalakinoside, mansonine, strebloside, hydrocoitisone, betamethasone, dexamethasone, non-steroidal substances (NSAIDS) such as fenoprofen, ibuprofen, indomethacin, naproxen, phenylbutazone and other antiviral agents such as acyclovir, ganciclovir and zidovudin, clotrimazol, flucytosin, griseofulvin, ketoconazol, miconazol, nystatin, terbinafin, anti-protozoal agents such as chloroquine, mefloquine, quinine, furthermore natural terpenoids such as hippocaesculin, barringtogenol-C21-angelate, 14-dehydroagrostistachine, agroskerin, agrostistachin, 17-hydroxyagrostistachin, ovatodiolides, 4,7-oxycycloanisomelic acid, baccharinoides B1, B2, B3 and B7, tubeimoside, bruceantinoside C, yadanzioside N and P, isodeoxyelephantopin, tomenphantopin A and B, coronarin A, B, C and D, ursolic acid, hyptatic acid A, iso-iridogermanal, maytenfoliol, effusantin A, excisanin A and B, longikaurin B, sculponeatin C, kamebaunin, leukamenin A and B, 13,18-dehydro-6-alpha-senecioyloxychaparrin, taxamairin A and B, regenilol, triptolide, furthermore cymarin, hydroxyanopterin, protoanemonin, cheliburine chloride, sinococulin A and B, dihydronitidin, nitidin chloride, 12-beta-hydroxypregnadiene 3,20-dione, helenalin, indicin, indicin-N-oxide, lasiocarpin, inotodiol, podophyllotoxin, justicidin A and B, larreatin, malloterin, mallotochromanol, isobutyrylmallotochromanol, maquiroside A, marchantin A, maytansin, lycoridicin, margetin, pancratistatin, liriodenin, bisparthenolidin, oxoushinsunin, periplocoside A, ursolic acid, deoxypsorospermin, psycorubin, ricin A, sanguinarin, manwuweizic acid, methylsorbifolin, sphatheliachromen, stizophyllin, mansonin, strebloside, dihydrousambaraensin, hydroxyusambarin, strychnopentamin, strychnophyllin, usambarin, usambarensin, liriodenin, oxoushinsunin, daphnoretin, lariciresinol, methoxylariciresinol, syringaresinol, sirolimus (rapamycin), somatostatin, tacrolimus, roxithromycin, troleandomycin, simvastatin, rosuvastatin, vinblastin, vincristin, vindesin, teniposide, vinorelbin, tropfosfamid, treosulfane, tremozolomide, thiotepa, tretinoin, spiramycin, umbelliferon, desacetylvismion A, vismion A and B, and zeorin.

The group of therapeutic agents that act against cancer can also be used.

The active substance can be applied in its pure form or together with a polymer. Preferably, dipping or spraying methods are used to apply the active substance.

Furthermore, the anti-proliferative, anti-inflammatory and/or anti-mycotic active substance can be embedded into a polymer matrix or can be situated under or also on a polymer matrix.

Furthermore, another polymer biostable or biodegradable layer, in addition to the polymer matrix, can be situated on the implant. This layer, too, can contain an anti-proliferative, anti-inflammatory and/or anti-mycotic active substance, which can be the same as or different from the active substance in the polymer matrix.

Preferred active substances that can be situated on the surface of the implant are selected from the group consisting of anti-inflammatory substances and, in particular, the corticosteroids. The following substances can be used as biostable or biodegradable polymers and/or polymers for the polymer matrix:

polyvalerolactones, poly-ε-decalactones, polylactonic acid, polyglycolic acid, polylactides, polyglycolides, copolymers of polylactides and polyglycolides, poly-ε-caprolactone, polyhydroxybutyric acid, polyhydroxybutyrates, polyhydroxyvalerates, polyhydroxybutyrates-co-valerates, poly(1,4-dioxan-2,3-diones), poly(1,3-dioxan-2-ones), poly-para-dioxanones, polyanhydrides, polymaleic acid anhydrides, polyhydroxymethacrylates, fibrin, polycyanoacrylates, polycaprolactondimethylacrylates, poly-β-malic acid, polycaprolactone butylacrylates, multi-block polymers of oligocaprolactondioles and oligodioxanondioles, polyetherester multi-block polymers of PEG and polybutylene terephtalate, polypivotolactones, polyglycolic acid trimethyl carbonates, polycaprolactone glycolides, poly(γ-ethylglutamate), poly(DTH-iminocarbonate), poly(DTE-co-DT-carbonate), poly(bisphenol A-iminocarbonate), polyorthoester, polyglycolic acid trimethylcarbonates, polytrimethyl carbonates, polyiminocarbonates, poly(N-vinyl)-pyrrolidone, polyvinyl alcohols, polyesteramides, glycolated polyesters, polyphosphoesters, polyphosphazenes, poly[p-carboxyphenoxy)propane], polyhydroxypentanic acid, polyanhydrides, polyethylene oxide propylene oxide, soft polyurethanes, polyurethane with amino acid radicals in the backbone, polyetheresters such as polyethylene oxide, polyalkenoxalates, polyorthoesters as well as the copolymers, lipids, carrageenanes, fibrinogen, starch, collagen, protein-based polymers, polyamino acids, synthetic polyamino acids, zein, polyhydroxyalkanoates, pectinic acid, actinic acid, carboxymethylsulfate, albumin, hyaluronic acid, chitosan and its derivatives, heparansulfate and its derivatives, heparins, chondroitinsulfate, dextran, β-cyclodextrins, copolymers with PEG and polypropylene glycol, gum arabic, guar, gelatin, collagen, collagen-N-hydroxysuccinimide, lipids, phospholipids, polyacrylic acid, polyacrylates, polymethylmethacrylate, polybutylmethacrylate, polyacrylamide, polyacrylonitriles, polyamides, polyetheramides, polyethylene amine, polyimides, polycarbonates, polycarbourethanes, polyvinylketones, polyvinylhalogenides, polyvinylidene halogenides, polyvinylethers, polyisobutylenes, polyvinyl aromatics, polyvinylesters, polyvinylpyrollidones, polyoxymethylenes, polytetramethylene oxide, polyethylene, polypropylene, polytetrafluorethylene, polyurethanes, polyetherurethanes, silicone-polyetherurethanes, silicone-polyurethanes, silicone-polycarbonate urethanes, polyolefin elastomers, polyisobutylenes, EPDM rubbers, fluorosilicones, carboxymethylchitosanes, polyaryletheretherketones, polyetheretherketones, polyethylenterephtalate, polyvalerates, carboxymethylcellulose, celluloses, rayon, rayontriacetates, cellulosenitrates, celluloseacetates, hydroxyethylcelluloses, cellulosebutyrates, celluloseacetate butyrates, ethylvinylacetat copolymers, polysulfons, epoxy resins, ABS resins, EPDM rubbers, silicones such as polysiloxanes, polydimethylsiloxanes, polyvinylhalogens and copolymers, celluloseethers, cellulosetriacetates, chitosans and copolymers and/or mixtures of the aforementioned polymers.

Several features of the present invention can be summarized as follows: No additional surgeries are required for explanation of the functional implant. No residues remain in the body. The degradation of the functional implant is controlled in a defined manner. In particular, the degradation can be slowed down, or only started once it is actually practical or necessary physiologically. It is also possible to implement time-controlled, local delivery of active substances in the body using the present invention.

BRIEF DESCRIPTION OF THE DRAWINGS

Various aspects of the present disclosure are described hereinbelow with reference to the accompanying figures.

DETAILED DESCRIPTION

Figure 1:
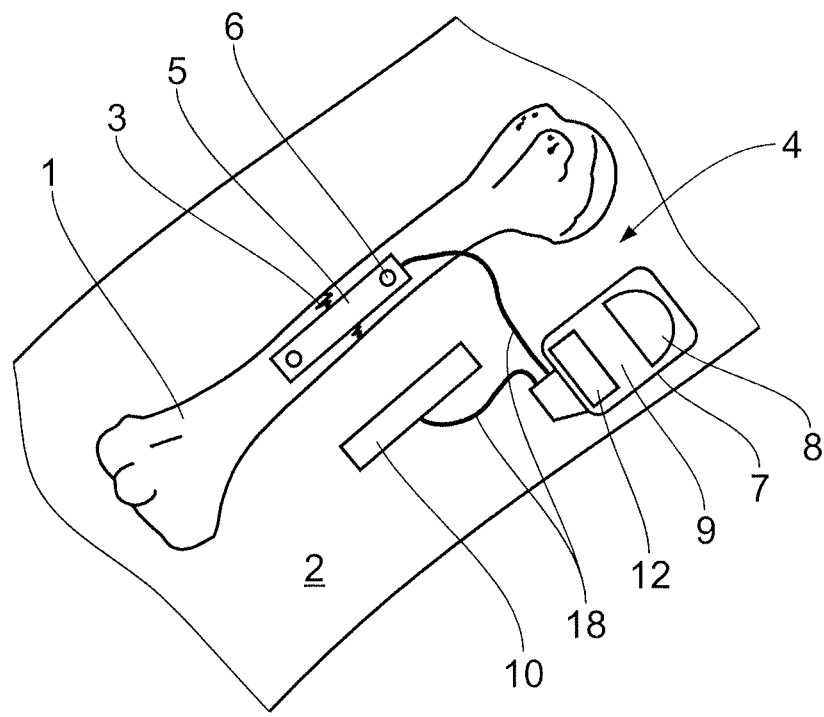
FIG. 1 is a schematic view of a first exemplary embodiment of a body part with a bone fracture and implant system.

FIG. 1 schematically shows a bone 1 in an extremity 2 of a person has suffered from a fracture 3. This fracture 3 is medically treated with an implant system 4, which system has a bone splint 5 with attachment screws 6 as the main components of the functional implant. This implant covers the fracture 3 of the bone 1 in order to immobilize and stabilize the bone fragments so that the bone fragments can grow back together. The bone splint 5 and attachment screws 6 are produced from a metal material that can be degraded by the extremity 2 of the body of the implant wearer, such as iron, magnesium, zinc, or tungsten, or a suitable alloy of these materials, for example.

Figure 4:
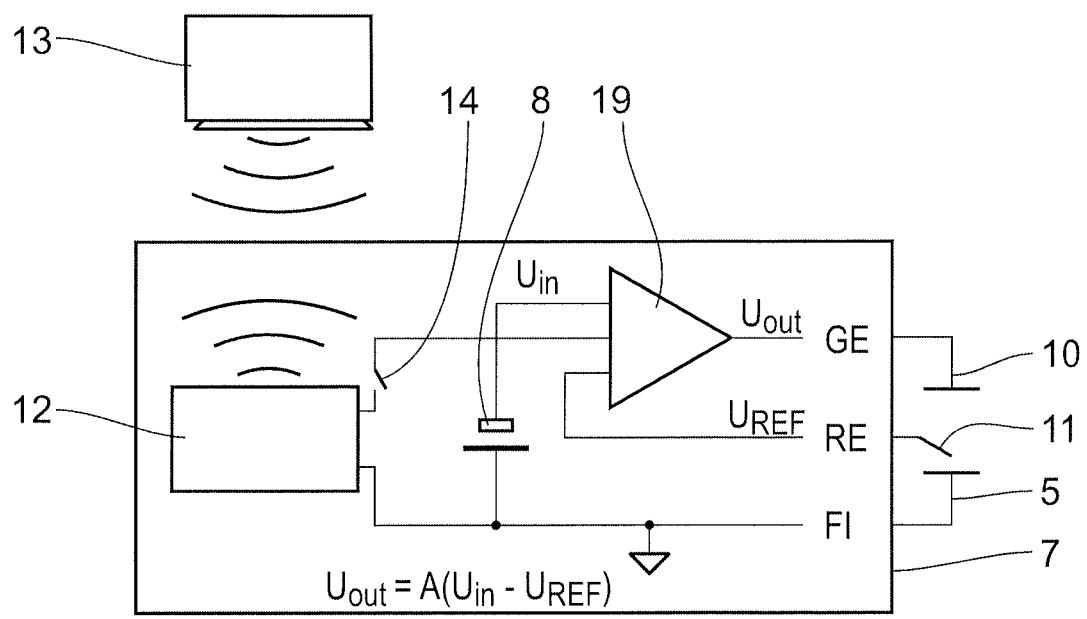
FIG. 4 is a circuit diagram for one exemplary embodiment of the implant system.
Figure 6:
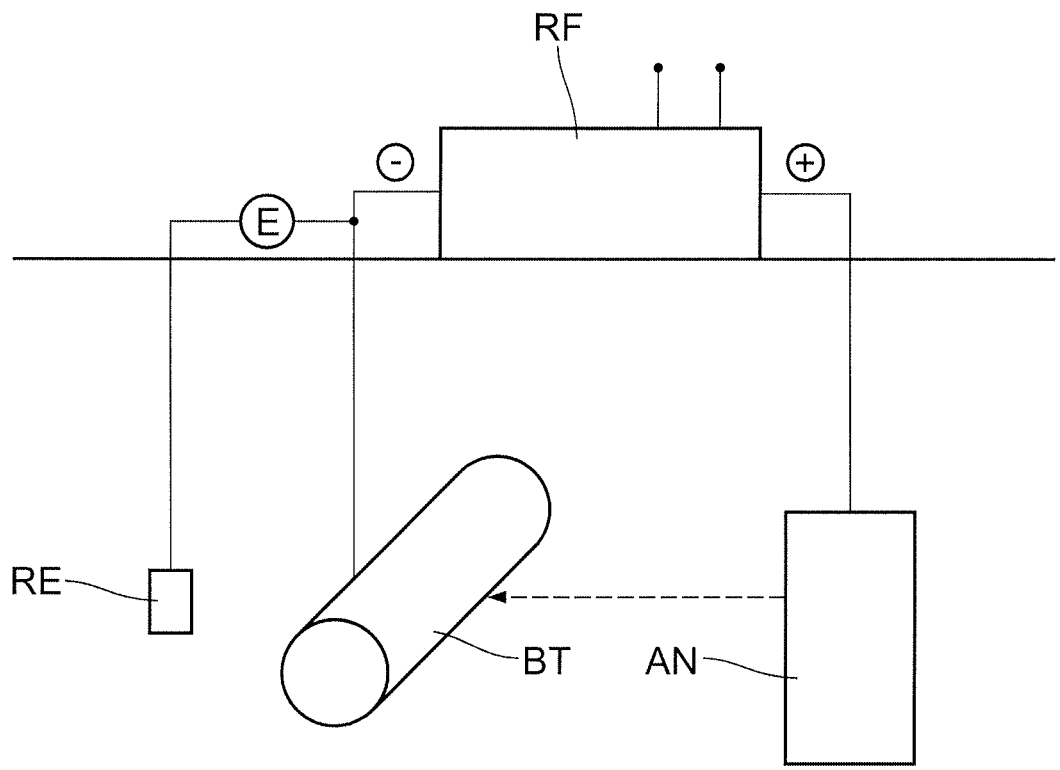
FIG. 6 is a schematic diagram of a cathodic protection system.
Figure 7:
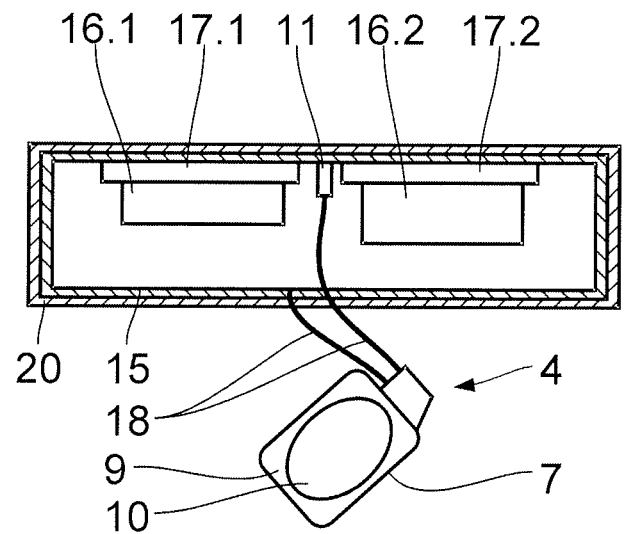
FIG. 7 is a schematic view of a second exemplary embodiment of a depot implant.

The second main component of the implant system is a control device 7, which is structured, for example, in the manner of a heart pacemaker. To provide power, a battery 8 is integrated into the control device 7. This battery is integrated into a housing 9 of the control device 7, which consists of a titanium alloy, for example. Furthermore, a counter-electrode 10 is provided, which consists of platinum. Between the control device 7, on the one hand, and the bone splint 5 and the counter-electrode 10, on the other hand, connection lines 18 are provided, with which a polarization voltage $U_{out}$ (see FIG. 4) can be applied between the bone splint 5 with its attachment screws 6, on the one hand, and the counter-electrode 10, on the other hand. Using this polarization voltage $U_{out}$, the degradation behavior of the bone splint 5 with its attachment screw 6 can be controlled such that when a corresponding polarization voltage $U_{out}$ is applied, the bone splint 5 with the attachment screws 6 is cathodically protected against degradation, in accordance with the electrochemical voltage conditions as shown in FIGS. 4, 6, and 7.

Figure 2:
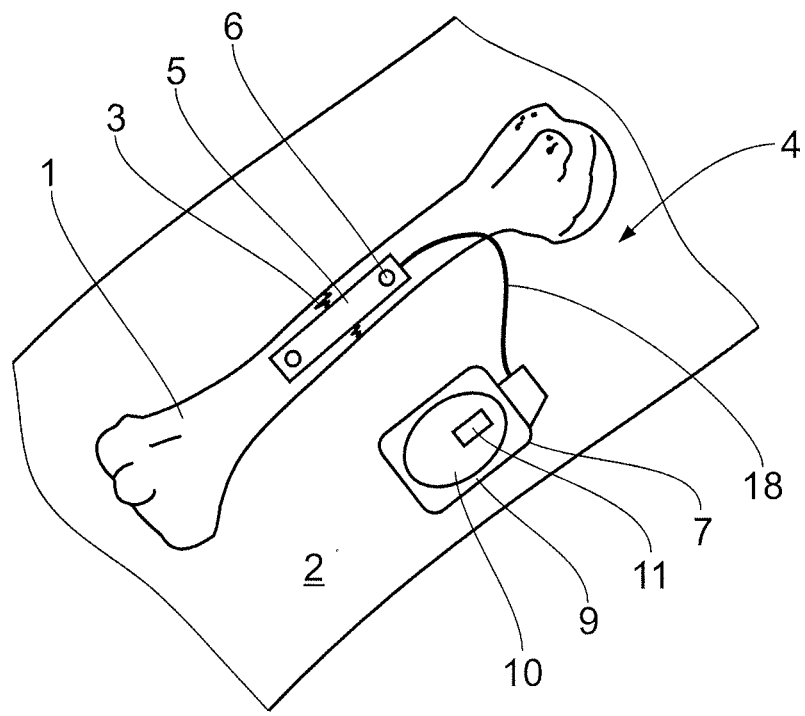
FIG. 2 is a schematic view of a second exemplary embodiment of a body part with a bone fracture and implant system.
Figure 3:
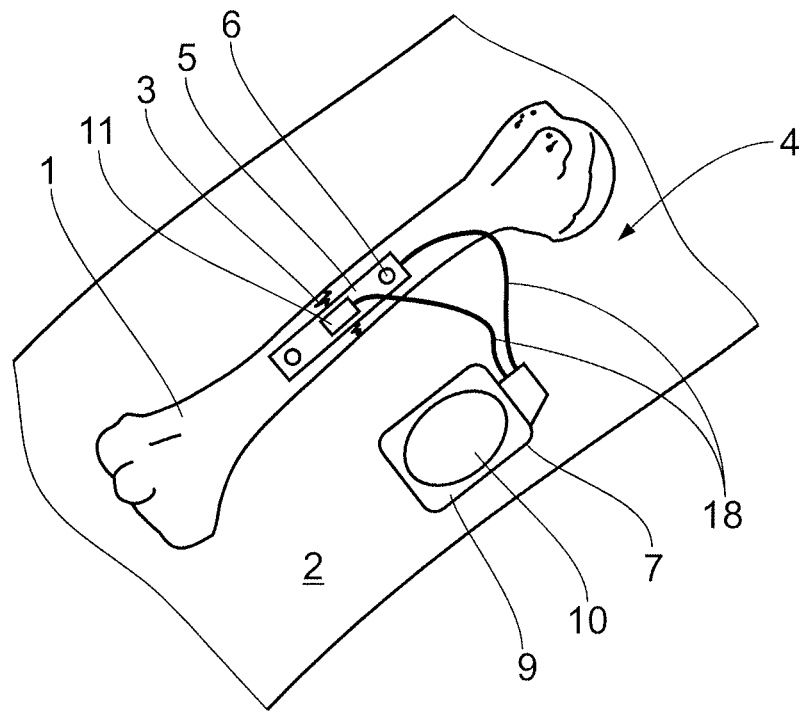
FIG. 3 is a schematic view of a third exemplary embodiment of a body part with a bone fracture and implant system.

In the exemplary embodiments according to FIGS. 2 and 3, the counter-electrode 10 is structured as a section of the housing 9. Furthermore, a reference electrode 11 is provided which is embedded into the counter-electrode 10 in an insulated manner in the case of the exemplary embodiment shown in FIG. 2. The voltage $U_{REF}$ that is actually applied at the functional implant can be determined using the reference electrode 11. The determination of the voltage $U_{REF}$ that is actually applied is necessary for regulation of the system. Namely, the voltage $U_{out}$ applied between the counter-electrode 10 and the functional implant, which allows the current I to flow from the counter-electrode 10 to the functional implant by way of the tissue, since a certain voltage drop $U_{IR}$ (IR drop) occurs as the result of the electrical resistance of the tissue R, which leads to the result that $U_{in}$ and $U_{REF}$ are not equal, and for this reason, the voltage $U_{out}$ has to be corrected by way of an amplifier 19 (see FIG. 4). The tissue resistance generally changes over the implantation period since the tissue that surrounds the functional implant and the counter-electrode 10 changes over the course of time.

The reference electrode 11 has a constant potential in vivo and no significant currents (other than those needed for measuring) flow over it. Materials such as Pt, PtIr, gold, carbon, or the like, are possible for the reference electrode 11.

The location of the reference electrode 11 is preferably selected to be spatially close to the functional implant. Here, an exemplary embodiment would be a PtIr sheet having an area of a few square millimeters, which is directly integrated into the control device 7 by means of a glass or ceramic passage through the housing 9, as shown in FIG. 2. Another exemplary embodiment would be a reference electrode 11 structured as a PtIr sheet having an area of a few square millimeters, which is applied directly on the bone splint 5, for example, glued on, with a connection line 18 to the control device (see FIG. 3). What is important is that in both cases, there is no short-circuit to the counter-electrode 10 and to the functional implant 5, respectively.

Aside from the reference electrode, other sensors can also be used. For example, the pH and the temperature can be recorded. Likewise, micro-arrays can be connected which sensitively responsive to biological factors such as inflammations.

As soon as the degradation of the bone splint 5 with its attachment screws 6 is supposed to proceed, the polarization voltage $U_{out}$ must be lowered or turned off entirely. For this, it is sufficient if the connection line 18 between control device 7 and bone splint 5 is interrupted, using a small operation. As soon as it is certain that polarization voltage is no longer required, the control device 7 is explanted.

As is evident from FIG. 4, the reference electrode 11 allows measuring the voltage $U_{REF}$ that is actually applied, in this connection, which is compared with the desired voltage $U_{in}$. If $U_{REF}$ and $U_{in}$ are different, the desired sameness is achieved by means of a corresponding adaptation of the voltage $U_{out}$ by means of the amplifier 19. Furthermore, the control device 7 can have a telemetric data transmission unit 12 which can be used to collect measurement data concerning the status of the functional implant, in other words, essentially of the bone splint 5 by means of sensors, not shown in any detail, and transmit the measurement data to an external base unit 13. From there, control data for controlling the voltage $U_{in}$ generated by the battery 8 and thus the polarization voltage $U_{out}$, both with regard to its value and the time progression, can be input. Accordingly, the polarization voltage $U_{out}$ can also be turned off entirely, by way of a switch 14 of the control device 7. A complete Home Monitoring System can be implemented with these functionalities.

Figure 5:
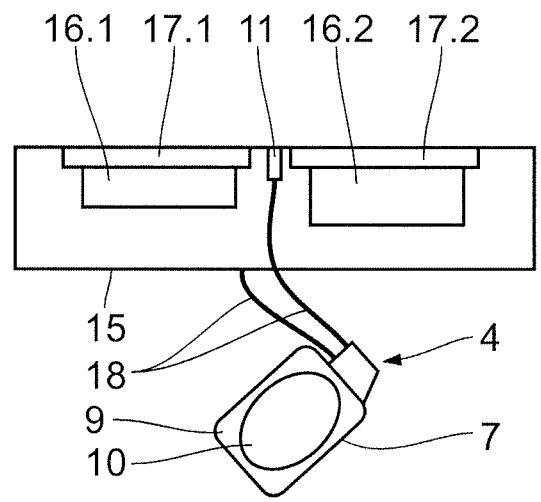
FIG. 5 is a schematic view of a first exemplary embodiment of a depot implant.

FIG. 5 shows an exemplary embodiment of the implant system 4 in which a depot implant 15, having multiple depot chambers 16.1, 16.2, is provided as the functional implant. These chambers are filled with different active substances, in each instance, and closed off with a cover 17.1, 17.2 composed of different degradable metal materials. The covers 17.1, 17.2 in turn are connected with a control device 7 of the type explained hereinabove using FIGS. 1 and 2, which can generate a polarization voltage $U_{out}$ between the counter-electrode 11 and the covers 17.1, 17.2 to control the degradation behavior of the covers 17.1, 17.2. Accordingly, release of the active substances in the depot chambers 16.1, 16.2 can be adjusted in a defined manner.

With reference to FIG. 6, the degradation behavior of degradable metal materials can be explained as follows.

Cathodic corrosion protection can be achieved in two ways:
a) by means of the use of sacrificial anodes, or
b) by means of external current anodes, i.e., outside current anodes (ICCP or Impressed Cathodic Current Protection).

In the case of method a), a very reactive ancillary metal is directly connected to the metal to be protected. In this connection, the ancillary material forms the anode of the system. The difference of the free corrosion potentials between the anode and the material to be protected causes a current flow through the electrolyte coming from the anode. The potential difference is determined by means of the relative position of the metals used in the electrochemical voltage series in the electrolyte used.

The external current technique shown in FIG. 6, according to method b), is generally used for protection of buried pipelines and on ship hulls that are exposed to seawater. In this connection, a direct current circuit is used to apply an electrical current to the metallic structure. The minus pole of the power source RF is connected with the metal that is supposed to be protected. The plus pole is connected with an additional anode AN that is situated in the same medium in order to close the circuit. The electrical current charges the structure with excess electrons and thereby changes the electrode voltage to the negative direction until the immunity region has been reached. In this connection, it is important that the anode AN and the cathode KA are completely separate from one another so that a flow of current through the medium between the electrodes of the anode to the cathode can take place. The function of the reference electrode RE is to monitor the electrode voltage of the protected structure, a buried pipeline in the case of this example, in order to ensure that the immunity region is reached. The reference electrode RE is designed in such a manner that it has a constant potential and no current flows by way of it. The rectifier DC-R acts as a voltage supply part and is employed so that the potential of the structure is sufficiently negative to reach the immunity region, which is regulated by the reference electrode RE.

FIG. 7 shows a depot system similar to the one shown in FIG. 5. In this regard, reference can be made to the description there. In contrast to this, partial or also complete coating or mantling of the entire implant system, or even only of parts of it, is provided. Possibilities for this are polymers as well as metallic and ceramic layers or layer systems 20. In this connection, coatings or layer systems 20 that are degradable in vivo are preferably used on the functional implant 15, while coatings or layer systems 20 that are not degradable in vivo can also be used on the side of the control device 7 and the connection lines 18, so that these parts of the implant system can be explanted again later.

Furthermore, the coatings 20 can be designed in such a manner that the coatings can release at least one therapeutic agent or multiple therapeutic substances or pharmacologically active substances having one or more time progressions.

All patents, patent applications and publications referred to herein are incorporated by reference in their entirety.

What is claimed is:

1. An implant system, comprising:
    a) a medical implant having a support, fixation, or hold function formed at least in part from a metal material that can be degraded by the body of the implant wearer, and
    b) a control device for controlling the degradation behavior of the medical implant, the control device having
    (i) at least one counter-electrode to the medical implant, the counter-electrode separate from the medical implant, and
    (ii) a voltage source adapted to apply a polarization voltage ($\Delta U$) between medical implant and counter-electrode, to control the degradation behavior of the medical implant.

2. The implant system of claim 1, further comprising at least one reference electrode for determining the voltage ($U_{ref}$) actually applied to the medical implant.

3. The implant system of claim 2, wherein the reference electrode comprises a material selected from the group consisting of platinum, platinum-iridium alloy, gold, and carbon.

4. The implant system of claim 2, wherein the reference electrode is on the medical implant.

5. The implant system of claim 1, wherein the voltage source comprises an implantable battery.

6. The implant system of claim 1, wherein the control device has a separately implantable counter-electrode.

7. The implant system of claim 1, wherein the counter-electrode is formed by the housing of the implantable control device.

8. The implant system of claim 1, wherein the voltage source is switchable either by means of cutting the line connection to the counter-electrode or by means of explantation.

9. The implant system of claim 1, wherein the medical implant comprises one or more metal materials of the group consisting of iron, magnesium, zinc, and tungsten, and alloys of the foregoing.

10. The implant system of claim 1, wherein the counter-electrode comprises either a precious metal or a degradable metal material that is more precious than the metal material of the medical implant.

11. An implant system, comprising:
    a) a medical implant formed at least in part from a metal material that can be degraded by the body of the implant wearer, and
    b) a control device for controlling the degradation behavior of the medical implant, the control device having
    (i) at least one counter-electrode to the medical implant, the counter-electrode separate from the medical implant,
    (ii) a voltage source adapted to apply a polarization voltage ($\Delta U$) between medical implant and counter-electrode, to control the degradation behavior of the medical implant, and
    (iii) a telemetrical data transmission unit.

12. An implant system, comprising:
    a) a medical implant formed at least in part from a metal material that can be degraded by the body of the implant wearer, and
    b) a control device for controlling the degradation behavior of the medical implant, the control device having
    (i) at least one counter-electrode to the medical implant, the counter-electrode separate from the medical implant,
    (ii) a voltage source adapted to apply a polarization voltage ($\Delta U$) between medical implant and counter-electrode, to control the degradation behavior of the medical implant, and
    (iii) a telemetrical data transmission unit,
        wherein either measurement data concerning the status of the medical implant or control data for controlling the polarization voltage ($\Delta U$) generated by the voltage source can be transmitted by way of the telemetrical data transmission unit.

13. An implant system, comprising:
    a) a medical implant formed at least in part from a metal material that can be degraded by the body of the implant wearer, the medical implant having at least one depot chamber filled with a therapeutic agent and
    b) a control device for controlling the degradation behavior of the medical implant, the control device having
    (i) at least one counter-electrode to the medical implant, the counter-electrode separate from the medical implant,
    (ii) a voltage source adapted to apply a polarization voltage ($\Delta U$) between medical implant and counter-electrode, to control the degradation behavior of the medical implant, and
    (iii) a telemetrical data transmission unit,
        wherein the depot chamber is at least partly formed by a metal material whose degradation can be controlled by means of the control device.

14. The implant system of claim 1, wherein either the medical implant or the control unit is coated with at least one coating that is permanent or degradable in vivo, from which coating at least one therapeutic agent or pharmacologically active substance can be released.

15. The implant system of claim 14, wherein the coating is selected from the group consisting of a polymer, a metal, an alloy and a ceramic.

16. An implant system, comprising:
   a) a medical implant formed at least in part from a metal material that can be degraded by the body of the implant wearer, and
   b) an implantable control device for controlling the degradation behavior of the medical implant, the control device having
      (i) at least one implantable counter-electrode to the medical implant, the counter-electrode separate from the medical implant, and
      (ii) an implantable battery adapted to apply a first polarization voltage ($\Delta U$) between the medical implant and the counter-electrode to reduce or prevent degradation of the medical implant at a first time and a second polarization voltage less than the first polarization voltage to increase degradation of the medical implant at a later time.

17. The implant system of claim 16, further comprising at least one reference electrode for determining the voltage ($U_{ref}$) actually applied to the medical implant.

18. The implant system of claim 17, wherein the reference electrode is embedded in the counter-electrode and wherein the reference electrode is insulated from the counter-electrode.

19. The implant system of claim 16, wherein the counter-electrode is formed by the housing of the implantable control device.

20. The implant system of claim 1, wherein the voltage source is adapted to apply a first polarization voltage ($\Delta U$) between the medical implant and the counter-electrode to reduce or prevent degradation of the medical implant at a first time and a second polarization voltage less than the first polarization voltage to increase degradation of the medical implant at a later time.

* * * * *